US007964074B1

(12) United States Patent
Sexton

(10) Patent No.: US 7,964,074 B1
(45) Date of Patent: Jun. 21, 2011

(54) ELECTROELUTION OF OLIGONUCLEOTIDES FROM GEL MATRICES

(75) Inventor: Joseph P. Sexton, Iowa City, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 83 days.

(21) Appl. No.: 12/391,405

(22) Filed: Feb. 24, 2009

Related U.S. Application Data

(60) Provisional application No. 61/031,217, filed on Feb. 25, 2008.

(51) Int. Cl.
G01N 27/447 (2006.01)
G01N 27/453 (2006.01)
(52) U.S. Cl. ........................................ 204/462; 204/613
(58) Field of Classification Search .................. 204/613, 204/614, 464
See application file for complete search history.

(56) References Cited

U.S. PATENT DOCUMENTS 4,747,918 A * 5/1988 Wassenberg, II ............. 204/462
2001/0032786 A1* 10/2001 Anderson et al. ............. 204/462

FOREIGN PATENT DOCUMENTS

JP 63-15148 A * 1/1988

OTHER PUBLICATIONS

JPO English language abstract of Ito JP 63015148 A patent published Jan. 22, 1988.*
English language translation of Itoh et al. JP 63-015148 A, translated Oct. 2010.*

* cited by examiner

Primary Examiner — Alex Noguerola
(74) Attorney, Agent, or Firm — John A. Petravich

(57) ABSTRACT

The invention can be used to purify and extract a target oligonucleotide from a gel substrate. The current invention extracts the target oligonucleotide so quickly that burn-off against the positive electrode is greatly reduced, yielding high optical density and purity. The need for an osmotic membrane or heavy salt/light salt barrier to capture the oligonucleotide is eliminated. The invention does not require a high salt concentration and therefore does not require a desalting column that is time-consuming and reduces yield.

8 Claims, 4 Drawing Sheets

```
                       SEQUENCE LISTING

<160> NUMBER OF SEQ ID NOS: 4

<210> SEQ ID NO 1
<211> LENGTH: 15
<212> TYPE: DNA
<213> ORGANISM: Artificial
<220> FEATURE:
<223> OTHER INFORMATION: Synthetic sequence for elution
<220> FEATURE:
<221> NAME/KEY: fluorescein-labeled
<222> LOCATION: (1)..(1)

<400> SEQUENCE: 1
tcgactcact tgtca                                                     15

<210> SEQ ID NO 2
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 2
cucaggaugg cggagcgguc u                                              21

<210> SEQ ID NO 3
<211> LENGTH: 19
<212> TYPE: DNA
<213> ORGANISM: Artificial
<220> FEATURE:
<223> OTHER INFORMATION: Synthetic oligonucleotide
<220> FEATURE:
<221> NAME/KEY: adenylated_allele
<222> LOCATION: (1)..(1)
<220> FEATURE:
<221> NAME/KEY: dideoxy-C
<222> LOCATION: (19)..(19)

<400> SEQUENCE: 3
actgtaggca ccatcaatc                                                 19

<210> SEQ ID NO 4
<211> LENGTH: 22
<212> TYPE: DNA
<213> ORGANISM: Artificial
<220> FEATURE:
<223> OTHER INFORMATION: Synthetic oligonucleotide

<400> SEQUENCE: 4
tggaatucuc gggcaccaag gu                                             22
```

ELECTROELUTION OF OLIGONUCLEOTIDES FROM GEL MATRICES

CROSS-REFERENCE TO RELATED APPLICATION

The present application claims priority under 35 U.S.C. §119(e) to U.S. provisional patent application No. 61/031,217 filed 25 Feb. 2008. The entire teachings of the above application are incorporated herein by reference.

FIELD OF THE INVENTION

This invention pertains to PAGE purification, specifically the post-electrophoresis extraction of the purified oligonucleotide from the gel substrate.

BACKGROUND OF THE INVENTION

The isolation of nucleic acids from agarose or polyacrylamide gels is a routine concern for biological labs. The methods of isolation have taken on greater importance as the study of small DNA and RNA molecules such as micro RNA (miRNA) molecules and small interfering RNA (siRNA) molecules has increased.

Traditional methods for the extraction of DNA from a gel, such as an agarose or polyacrylamide gel, are time-consuming, low-yielding or limited in their application. One method for purifying and extracting oligonucleotides from a gel is the "crush-and-soak" method. For example, a technician will remove the portion of gel containing DNA and crush it in a microcentrifuge tube using a plastic pipette tip, and incubate with constant shaking in an elution buffer (with a high salt concentration) at an elevated temperature. The gel pieces are then eliminated by centrifugation or by passing the mixture through a plug of siliconized glass wool. Finally, DNA is recovered by ethanol precipitation. The process takes several hours, requires utilizing a desalting column and typically retains only half of the desired product.

Another method of extraction is the use of dialysis tubing. The portion of the gel with the desired oligonucleotide product is placed in dialysis tubing with electrophoresis buffer, sealed and placed into an electrophoresis chamber. Applying an electric current will cause the oligonucleotide to migrate out of the gel, but it will be trapped within the bag. When the oligonucleotide is out of the gel, the flow of current is reversed for a few seconds to remove the oligonucleotide from the side of the tubing. The buffer containing the oligonucleotide is then collected and the oligonucleotide is precipitated with ethanol. This method is primarily reserved for the recovery of large (>5 kb) DNA fragments, and is even more time-consuming than the crush-and-soak method.

Oligonucleotides can also be recovered from a gel by use of certain types of silica gel particles. However, small (<100 bp) fragments of DNA are very difficult to elute from standard glass particles.

In the case of miRNAs, the isolation can be difficult. MiRNAs are small non-coding RNAs that are involved in post-transcriptional gene regulation (cf., Bartel, 2004). First identified in *C. elegans* just over a decade ago (Lee et al., 1993), miRNAs have been identified in virtually every metazoan and plant species examined Experimental evidence is rapidly accumulating that shows miRNAs to play key roles in processes such as cellular differentiation, cell death, and adipose storage as well as in disease processes such as cancer. Over the past few years, a number of investigators have reported on methods for cloning miRNAs from primary RNA sources (Elbashir et al., 2001; Lau et al., 2001; Pfeffer et al., 2003; Sunkar and Zhu, 2004.

The mass of non-coding small RNAs relative to the total RNA produced by a cell is vanishingly small. Thus, the process of isolating and cloning these RNAs (miRNAs are 21 nt to 23 nt in length) is critically dependent upon being able to both enrich and efficiently recover RNA species in the proper size range. One protocol that was developed involves two PAGE gel steps, each of which involves a crush and soak RNA purification from a gel slice and a subsequent desalting via a NAP-5 purification column (Devor et al., U.S. patent application Ser. No. 12/165,436). The desired RNA species at the outset has a low mass, and there is unavoidable loss of mass that accompanies the above purifications.

The current invention extracts the target oligonucleotide rapidly, thereby avoiding burn-off against the positive electrode, yielding high optical density and purity. The need for an osmotic membrane or heavy salt/light salt barrier to capture the oligonucleotide is eliminated. The invention does not require a high salt concentration and therefore does not require a desalting column that is time-consuming and reduces yield. These and other advantages of the invention, as well as additional inventive features, will be apparent from the description of the invention provided herein.

BRIEF SUMMARY OF THE INVENTION

The current invention permits the elution of a target oligonucleotide from the face of a gel or a portion of a gel (the gel or a portion thereof also referred herein as a "gel slice") containing the target oligonucleotide, and transferring the target oligonucleotide into a small amount of standard electrophoresis buffer in about ninety seconds. The invention apparatus is comprised of a lower chamber and a recovery chamber with a sealing lip (the apparatus is hereinafter referred to as the "eluter"). A portion of the gel containing the oligonucleotide is placed into the lower chamber, and the small recovery chamber with a sealing lip is held against the gel slice and filled with standard electrophoresis buffer. A positive electrode is immersed in the small amount of buffer. A measured amount of buffer is placed into the lower chamber which contains a negative electrode. A direct electric current is applied to the electrodes. The current causes the oligonucleotide to travel from the inside of the gel slice out through the face of the slice and into the buffer in the recovery chamber. After about ninety seconds, the current is removed. The buffer in the recovery chamber, which now contains the target oligonucleotide, is then aspirated. The oligonucleotide-containing buffer can then be dispensed into a container for further purification or assay measurements. There is no need for crushing, soaking or extensive dry-down phases of the extraction process. Therefore the purification time is reduced to a fraction of the time (ninety seconds compared to 5-14 hours).

DETAILED DESCRIPTION OF THE INVENTION

The current invention permits the elution of a target oligonucleotide from a gel slice or the face of the gel slice into a small amount of standard electrophoresis buffer in about ninety seconds. The invention apparatus is comprised of a master well with a lower chamber, and a recovery chamber with a sealing lip (the invention is hereinafter referred to as the "eluter"). The eluter may have multiple lower and recovery chambers, e.g., parallel lower chambers and parallel recovery chambers that could align with an automated aspirating device.

Figure 1:
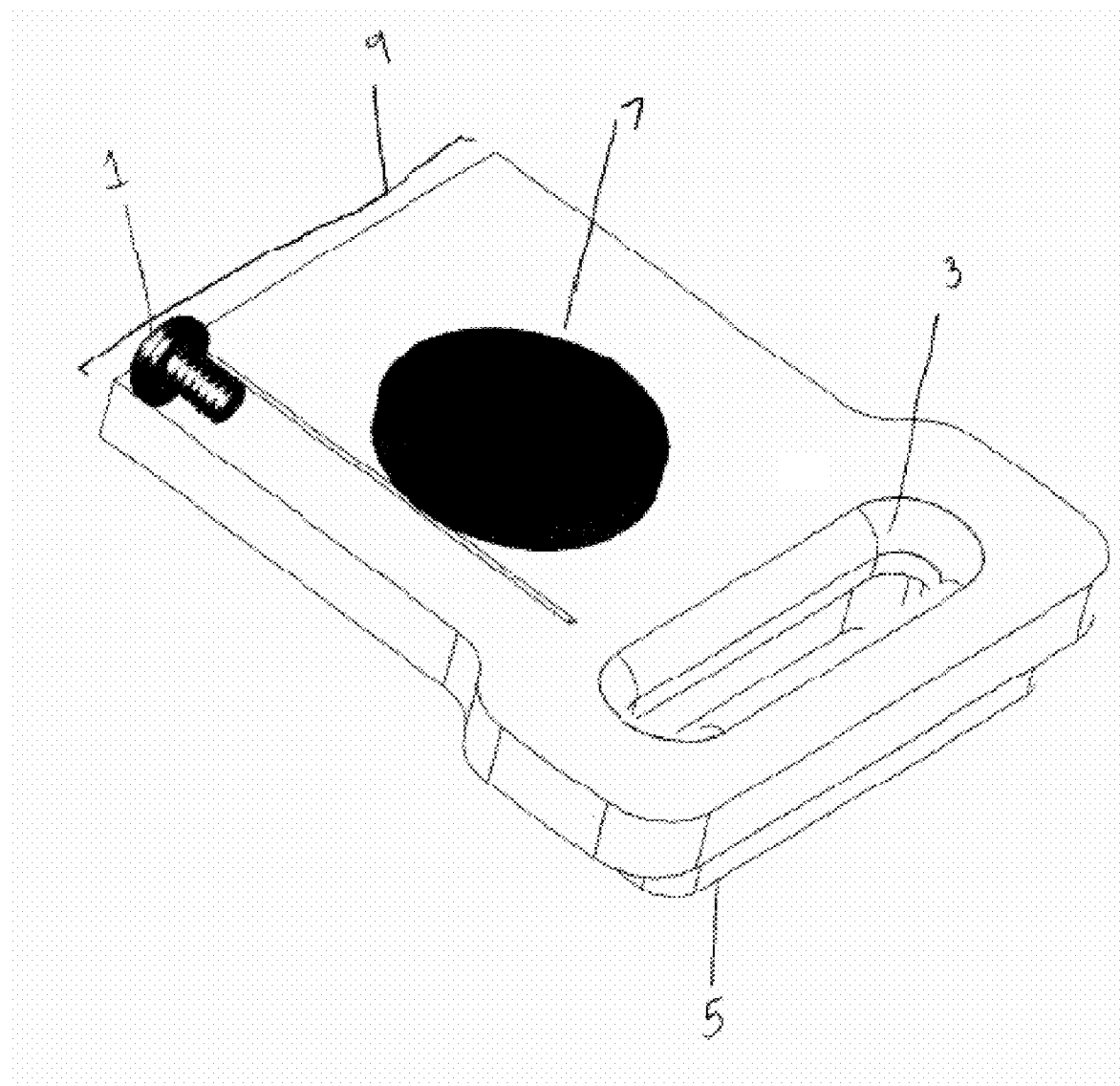
FIG. 1 shows a recovery well portion of the eluter. The recovery well will magnetically attach to the top of the master well and provides a well to collect the target oligonucleotide to be eluted.

FIG. 1 shows a recovery well portion 9 of the eluter. A positive current is run through an electrode 1 through the recovery well 3 and into the standard gel box buffer solution in the recovery well. A lip 5 is located on the bottom of the recovery well, and the lip will make contact with the gel sample. The gel sample will act as a gasket, keeping buffer solution in the recovery well. A magnet 7 will be drawn to a magnet on a master well containing the lower chamber (FIG. 2) to facilitate the desired placement of the recovery well onto the master well.

Figure 2:
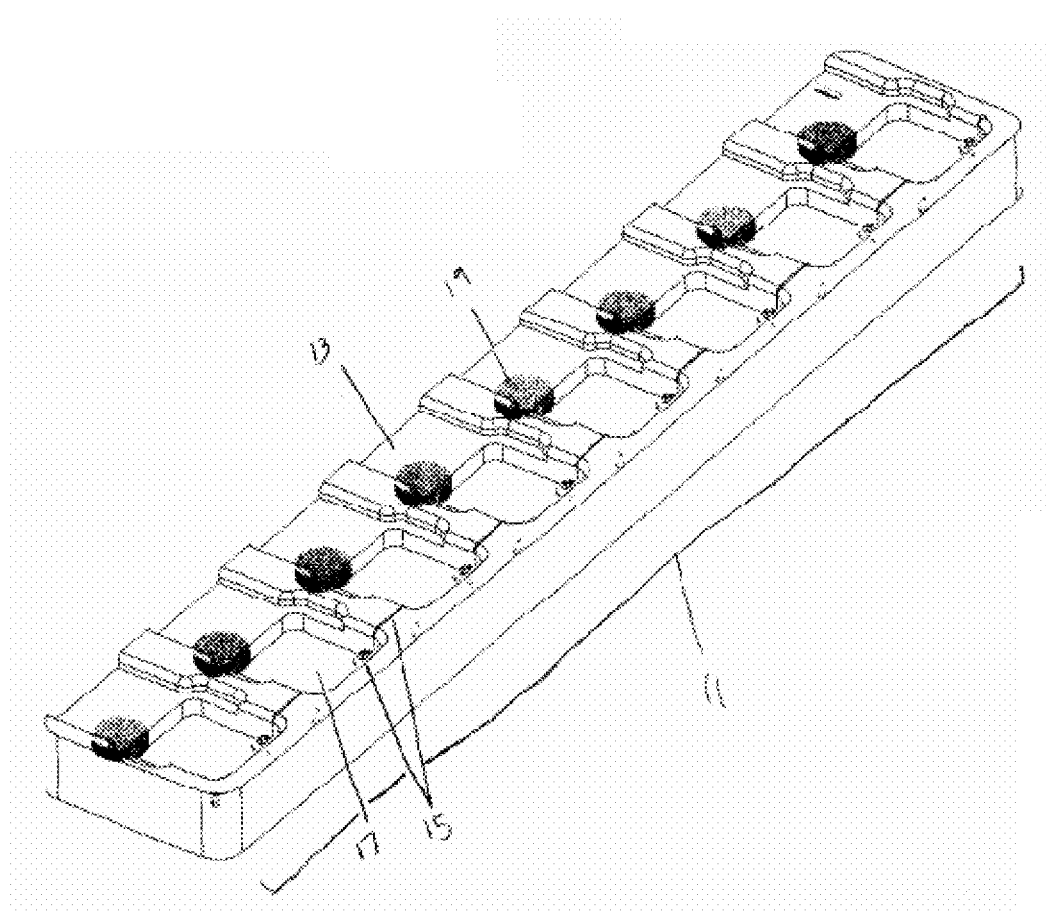
FIG. 2 shows a master well portion of the eluter.

FIG. 2 shows a master well 11 containing 8 lower chambers 17 for multiple elutions. The recovery well sits inside an indented area 13 of the master well. The lower chambers contain standard buffer solution, and the gel sample is placed in the lower chamber. A direct electric current of approximately 150 volts d.c. is applied to the electrodes 15 that are located in the lower chambers. The current causes the oligonucleotide to travel from the inside of the gel slice out through the face of the slice and into the buffer in the recovery chamber. After about ninety seconds, the current is removed. The buffer in the recovery well would then contain the target oligonucleotide which can be aspirated for further processing or measurements. A magnet 19 will attract the magnet from the recovery well portion to provide the desired placement of the recovery well.

Figure 3:
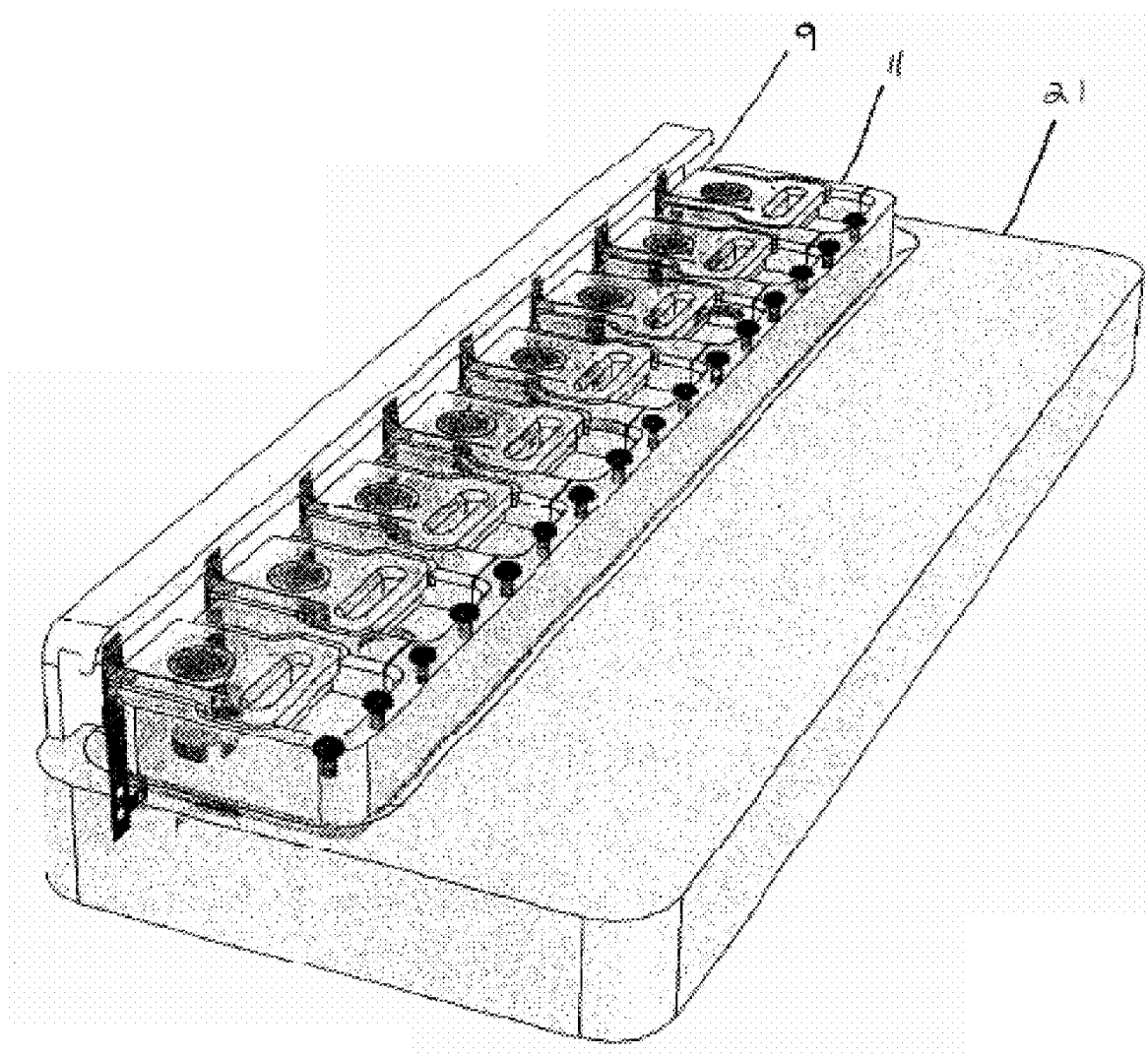
FIG. 3 shows a complete eluter unit sitting in a base used for automated elution. The gel sample containing the target oligonucleotide to be eluted will sit in the master well and electric current will provide the means to move the oligonucleotide from the gel into the recovery well.

FIG. 3 shows a complete eluter sitting on a base 21 used to assist the loading of the eluter into an automated system. The automated system may contain one or more aspirators to remove the oligonucleotide for post-elution steps.

In one embodiment, a piece of gel about 1"×½" is removed from a standard 1/16" gel slab. This gel piece is inserted into the eluter. In another embodiment, the eluter contains multiple recovery chambers wherein a larger gel slice, or a whole gel, with multiple target oligonucleotides can be eluted simultaneously. A separate recovery chamber can be located above each band of target oligonucleotide. This would eliminate the need to slice apart a gel. Alternatively, the larger eluter with a multi-recovery chamber format can simply provide for multiple gel pieces to be run at the same time.

There is no functional requirement to place the recovery well above the lower chamber. In alternative embodiments, the currents are reversed and the recovery can take place in a lower well. Alternatively, the wells could be placed adjacent to each other, wherein the gel still provides a barrier between a first buffer area with a negative current and a second buffer area with a positive current.

In one embodiment a direct electric current of about 50 to 200 volts d.c. can be used. In a further embodiment, a direct electric current of about 100 to 200 volts d.c. can be used, and in another embodiment a direct electric current of about 125 to 175 volts d.c. can be used, and in a further embodiment a direct electric current of about 150 volts d.c. can be used. By lowering or raising the current, one can control how quickly the target oligonucleotide will be eluted into the recovery well.

In one embodiment, a magnet is used to attach the recovery well to the master well in the desired orientation. Other means of attachment could be used, such as a clasp, a weight, a clip, a screw, a pin or rod, or the weight of the recovery well itself will be adequate to achieve the desired positioning.

Because the target oligonucleotide is captured in a small amount of buffer in a small recovery chamber with little need for multiple post-extraction steps, the eluter is ideal for providing an extracting component in a larger automated system. Because one embodiment of the eluter could accept a full gel slab with multiple target oligonucleotides, an automated system could perform all operations from the initiating of the gel run through the complete extraction of target oligonucleotides.

The following examples further illustrate the invention but, of course, should not be construed as in any way limiting its scope.

EXAMPLE 1

This example demonstrates the ability of a multi-eluter to efficiently elute target oligonucleotides from gel samples.

Eight 15-mer oligonucleotide samples labeled with fluorescein containing the following sequence were run on a 15% polyacrylamide gel.

SEQ ID No. 1: 5'-F-TCGACTCACT TGTCA-3' (F=fluorescein)

700 µl of standard buffer solution (1M Tris, 1M Boric Acid, and 30 nM EDTA, diluted 1:10 with purified water) was loaded into the master well lower chamber, and 300 µl standard buffer solution was loaded into the recovery well. 145-150 volts at 70 mAmps of current ran through the electrodes and the recovery well for 90 seconds. The stained oligonucleotide could be observed moving through the gel and into the recovery well. An 8-tip Packard/Janus robot aspirated the recovery well buffer containing the target oligonucleotide.

OD readings were performed using a BioTek PowerWave™ spectrophotometer, and the CE readings were performed using an Oligo PRO 96XT HT-CE. The following table lists the resulting ODs and CE % obtained for the eight samples

TABLE 1

Yield and purity of multi-eluter samples

| Sample | OD | CE % |
|---|---|---|
| 1 | 1.6 | 94.4 |
| 2 | 1.9 | 94.4 |
| 3 | 2.2 | 91.4 |
| 4 | 2.1 | 96.0 |
| 5 | 1.6 | 92.2 |
| 6 | 1.8 | 90.7 |
| 7 | 1.5 | 96.7 |
| 8 | 1.5 | 93.7 |

Typical yields for crush and soak methods can be as low as 0.5 OD, with a purity of about 88%. Therefore, the present invention can provide a greater yield and a greater purity while requiring only a fraction of the time needed in the crush-and-soak method.

EXAMPLE 2

The following example demonstrates the usefulness of the eluter in the recovery of micro RNA. The example was designed to also determine whether cellular RNAs recovered from a PAGE gel slice using the eluter would still attach to two linkers creating a chimeric DNA/RNA nucleic acid required for cloning. The following sequence was run on a gel using the same procedure as Example 1.
SEQ ID No. 2: 5'-rCrUrCrArGrGrArUrGrGrCrGr-GrArGrCrGrCrGrUrCrU-3'

RNA linkering. Once the enriched small RNA fraction has been recovered from the acrylamide gel slice using the eluter, the small RNAs are ligated with a 3' and a 5' linker in two separate, sequential reactions. The first reaction is the 3' ligation. In order to avoid circularization of the RNA fragments, the 3' linker is ligated to the small RNAs using T4 RNA ligase in the absence of ATP. This reaction requires use of a pre-activated 5' adenylated (rApp) cloning linker with a 3' ddC end-block (Lau et al., 2001).

In an RNase-free 0.2 ml tube the following are added:

| Recovered small RNA fraction | y µl |
| 3' RNA linker (50 µM) | 1 µl |
| 10× Ligation Buffer | 2 µl |
| Ligation Enhancer (such as DMSO) | 6 µl |
| T4 RNA Ligase (1 U/µl) | 1 µl |
| IDT water | (10-y) µl |
| Total Volume | 20 µl |

The 10× Ligation Buffer is a reaction buffer. SEQ ID NO:3 is an example of a 3' linker that has been utilized in cloning. The Ban I restriction endonuclease site is underlined.
SEQ ID NO: 3 5'-rAppCTGTAGGCACCATCAAT/3ddC/-3'

The above reagents are incubated at 22° C. for two hours. Then 80 µl IDTE (pH 7.5) is added and the entire volume is transferred to an RNase-free 1.5 ml tube. 3 µl glycogen (10 mg/ml), 1/10 volume (10 µl) 3.0 M NaOAc and 2.5 volumes (250 µl)-20° C. 100% EtOH are added. The sample is mixed by inversion or vortexed briefly, and then placed at −80° C. for 30 min. The sample is centrifuged at 16000×g for 10 min. The supernatant is removed, and the pellet is dried completely and resuspended in 10 µl DNase/RNase/pyrogen-free water.

Page purification of 3'-linkered products. Any free 3'-linker present will compete with the linkered small RNAs for ligation in the subsequent 5' ligation step. Unreacted linkers are therefore removed by PAGE purification. Ligated RNAs are 40 nt long while the unligated 3' linker is 19 nt long. These sizes are easily resolved on a 12% denaturing (7M urea) polyacrylamide gel. The linkered RNAs are recovered using the same methods as employed during the enriched small RNA enrichment process performed earlier. The gel is stained with GelStar® and cut out 2 mm above and below the 40 nt band. The RNA is recovered using the eluter.

5' Linkering reaction. The 5' multiple restriction site (M.R.S.) linker is ligated to the 3' linkered small RNAs in the presence of 1.0 mM ATP. The M.R.S. contains five restriction sites and is therefore compatible with many cloning vectors. Several different 3' linkers can be utilized with this single 5'-linker. The Ban 1 3'-linker employed herein is similar to the "modban" sequence employed by Lau and Bartel (Lau et al., Science, 294:858-62, 2001) and contains a Ban-I restriction site. The following sequence is the M.R.S. linker employed in the present example.
SEQ ID NO:4 5' TGGAATrUrCrUrCrGrGrGrCrArCr-CrArArGrGrU 3'

The following are added to an RNase-free 0.2 ml tube:

| Recovered 3' linkered RNA fraction | y µl |
| 5' RNA linker (50 µM) | 1 µl |
| 10× Ligation Buffer | 2 µl |
| Ligation Enhancer | 6 µl |
| 10 mM ATP | 2 µl |
| T4 RNA Ligase (5 U/µl) | 1 µl |
| RNase/DNase/pyrogen-free water | (8-y) µl |
| Total Volume | 20 µl |

The ligation reactions are incubated at 22° C. for two hours. Following incubation, 80 µl IDTE (pH 7.5) is added and the entire volume is transferred to an RNase-free 1.5 ml tube. 3 µl glycogen (10 mg/ml), 1/10 volume (10 µl) 3.0 M NaOAc and 2.5 volumes (2500-20° C. 100% EtOH is then added. The sample is mixed by inversion or vortexed briefly and then placed at −80° C. for 30 min. The sample is then centrifuged at 16000×g for 10 min. and the supernatant is removed. The pellet is completely dried and resuspended in 10 µl nuclease/pyrogen-free water. It is not necessary to gel purify this reaction. If it is purified, it should be performed using the same protocol as was employed previously. The material was then resolved on a gel as in Example 1.

Figure 4:
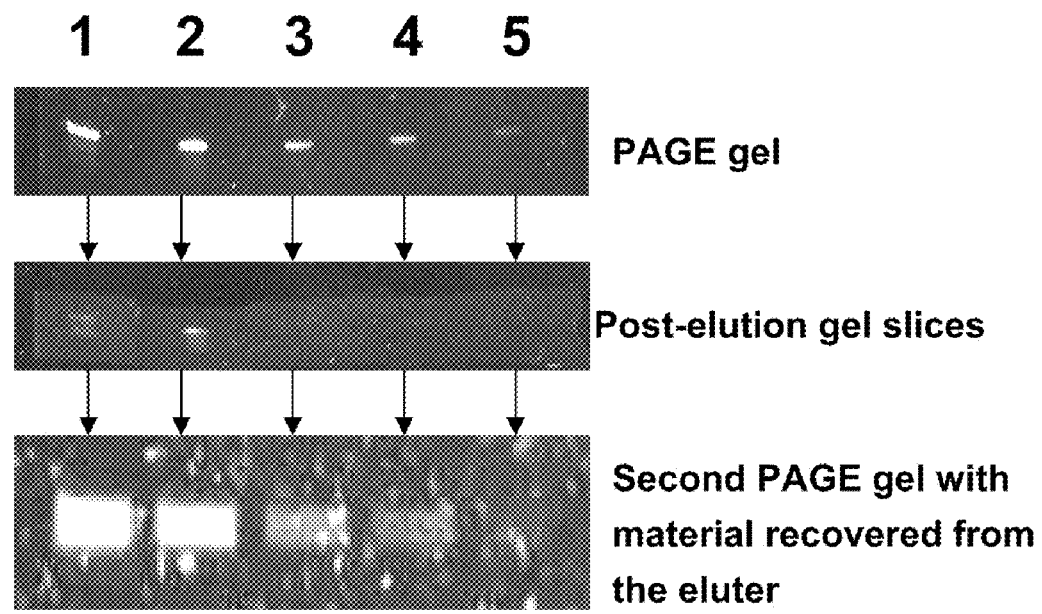
FIG. 4 is a set of three gels illustrating the effectiveness of the eluter. The top gel illustrates the initial RNA on a polyacrylamide gel, the middle gel slices illustrate the trace amount of RNA not eluted using the eluter, and the bottom gel illustrates the eluted gel containing the 3' and 5'-linkers.

The materials recovered from 15% denaturing PAGE gel slices efficiently accepted linkering in a manner suggesting that the elution process does not damage the RNAs in any way (see FIG. 4). The top gel in FIG. 4 illustrates the initial PAGE gel, and the middle gel in FIG. 4 illustrates the gel slices after the majority of the RNA has been extracted using the eluter. The lower gel depicts the chimeric RNA/DNA that was produced.

A second series of experiments was carried out to determine if any downstream processing was required following elution. The results showed that RNAs eluted from 15% denaturing PAGE gel slices in a 0.05×TBE buffer did not require desalting or any other subsequent processing for proper reactivity in the linkering steps of the microRNA cloning protocol. It was also determined that these RNAs would efficiently elute at 150 volts in three minutes.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An apparatus for the recovery of a target oligonucleotide in a gel sample, said apparatus comprising:
   a) a chamber for placement of the gel sample and a buffer solution;
   b) a source of electric current to provide a negative electric current to the chamber;
   c) a recovery well separate from the chamber wherein the gel sample forms a bottom of the recovery well, said recovery well capable of holding a buffer solution; and
   d) a second source of electric current to provide a positive electric current to the recovery well.

2. An apparatus of claim 1 wherein the apparatus contains more than one chamber and more than one recovery well.

3. An apparatus of claim 1 further comprising a recovery well aspirator.

4. An automated system for the loading and elution of a gel, comprising:
   a) a component for the loading of a sample into a gel;
   b) a component for the transfer of the gel to the apparatus of claim 1; and
   c) an aspirator.

5. The automated system of claim 4 wherein the apparatus of claim 1 has more than one chamber and more than one recovery well.

6. A method of removing a nucleic acid sample from a gel, the method comprising:
   a) excising a gel portion from the gel, said gel portion containing the nucleic acid sample;
   b) providing a negative charge to the gel portion;
   c) providing a recovery well, said recovery well being formed by the placement of a surface with an opening, wherein said opening sets against the gel portion and forms a seal to allow a buffer solution to sit in the opening against the gel portion;
   d) providing a buffer solution to the opening;
   e) providing a positive charge to the buffer solution; and
   f) collecting the buffer solution.

7. The method of claim 6 wherein the negative charge and the positive charge are provided for about 90 seconds.

8. The method of claim 6 wherein a current provided by the positive and negative charges is greater than 100 volts.

* * * * *